(12) United States Patent
Melamed

(10) Patent No.: US 9,005,292 B2
(45) Date of Patent: Apr. 14, 2015

(54) VERTEBRAL SPACER

(76) Inventor: Hooman M. Melamed, Marina del Rey, CA (US)

(*) Notice: Subject to any disclaimer, the term of this patent is extended or adjusted under 35 U.S.C. 154(b) by 310 days.

(21) Appl. No.: 13/104,477

(22) Filed: May 10, 2011

(65) Prior Publication Data
US 2012/0290089 A1   Nov. 15, 2012

(51) Int. Cl.
*A61F 2/44* (2006.01)
*A61B 17/86* (2006.01)
*A61F 2/30* (2006.01)

(52) U.S. Cl.
CPC ............ *A61F 2/442* (2013.01); *A61B 17/86* (2013.01); *A61F 2002/30265* (2013.01); *A61F 2002/30266* (2013.01); *A61F 2002/30281* (2013.01); *A61F 2002/30578* (2013.01); *A61F 2002/30787* (2013.01); *A61F 2002/30841* (2013.01); *A61F 2002/30843* (2013.01); *A61F 2310/00017* (2013.01); *A61F 2310/00023* (2013.01); *A61F 2310/00179* (2013.01)

(58) Field of Classification Search
USPC .............................. 623/17.11–17.16
See application file for complete search history.

(56) References Cited

U.S. PATENT DOCUMENTS

| | | | |
|---|---|---|---|
| 5,776,134 A | 7/1998 | Howland | |
| 5,928,232 A | 7/1999 | Howland et al. | |
| 6,132,430 A | 10/2000 | Wagner | |
| 6,776,798 B2 | 8/2004 | Camino et al. | |
| 7,066,960 B1 | 6/2006 | Dickman | |
| 7,608,107 B2 | 10/2009 | Michelson | |
| 7,635,380 B2 | 12/2009 | Zucherman et al. | |
| 7,867,277 B1* | 1/2011 | Tohmeh | 623/17.11 |
| 7,905,910 B2* | 3/2011 | Gerlach et al. | 606/291 |
| 7,909,869 B2 | 3/2011 | Gordon et al. | |
| 2007/0016205 A1* | 1/2007 | Beutter et al. | 606/69 |
| 2007/0219635 A1* | 9/2007 | Mathieu et al. | 623/17.16 |
| 2008/0243252 A1* | 10/2008 | Hansen et al. | 623/17.16 |
| 2009/0030520 A1* | 1/2009 | Biedermann et al. | 623/17.16 |
| 2010/0145459 A1* | 6/2010 | McDonough et al. | 623/17.16 |
| 2010/0161061 A1* | 6/2010 | Hunt | 623/17.16 |
| 2010/0217393 A1* | 8/2010 | Theofilos | 623/17.11 |
| 2011/0125266 A1* | 5/2011 | Rodgers et al. | 623/17.11 |
| 2011/0224671 A1* | 9/2011 | Koay et al. | 606/70 |

OTHER PUBLICATIONS

News Release, Medtronic, "Medtronic Introduces the Sovereign(TM) Spinal System for Lumbar Surgery", Memphis, TN, Dec. 18, 2009.
Prinout of Technique Guide for SynFix-LR System (website: http://products.synthes.com/) (Aug. 2010).

* cited by examiner

*Primary Examiner* — Jerry Cumberledge
*Assistant Examiner* — Nicholas Plionis
(74) *Attorney, Agent, or Firm* — Thomas, Karceski & Karmilovich, PC

(57) ABSTRACT

A vertebral spacer includes a body having a top side, a bottom side, a front side, and a rear side. The top side is configured to be positioned adjacent to a first vertebra and the bottom side is configured to be positioned against a second vertebra. First, second, third and fourth bores extend through the body. First and second compression fasteners disposable in the first and third bores, and first and second locking fasteners disposable in the second and fourth bores. The first compression fastener and the first locking fastener cooperate to apply and lock a first predetermined compression force between the body and the first vertebra. The second compression fastener and the second locking fastener cooperate to apply and lock a second predetermined compression force between the body and the second vertebra.

19 Claims, 14 Drawing Sheets

VERTEBRAL SPACER

CROSS-REFERENCE TO RELATED APPLICATION(S)

This is a first-filed Non-Provisional United States patent application and, therefore, does not rely on any other patent application for priority.

FIELD OF THE INVENTION

The present invention relates to a medical device. More specifically, the present invention concerns a spacer (or shim) that is insertable between spinal vertebrae to secure adjacent vertebrae to one another.

DESCRIPTION OF THE RELATED ART

The prior art illustrates several devices and methods that permit adjacent vertebrae to be connected to one another and, thereby, address any of a number of physical ailments.

U.S. Pat. No. 7,909,869 (hereinafter "the '869 patent") describes artificial spinal unit assemblies that are intended for insertion between adjacent vertebrae. The insert provides stability, flexibility, and proper biomechanical motion between the adjacent vertebrae. (The '869 patent at col. 1, lines 14-18.) The spinal implant is constructed to provide an anatomically correct range of motion. (The '869 patent at col. 1, lines 18-23.) The intervertebral implant 10 includes an upper body 12 and a lower body 14 in a substantially parallel planar configuration. (The '869 patent at col. 9, lines 55-57.) The upper body 12 includes an substantially concave inferior surface 16. (The '869 patent at col. 9, lines 65-66.) The lower body 14 has a channel in its superior surface 17. (The '869 patent at col. 9, lines 66-67.) An expandable joint resides within the channel 15 on the lower body. (The '869 patent at col. 10, lines 3-5.) The expandable joint insert 19 is lifted from the bottom of the channel 15 by means of an expansion screw 22. (The '869 patent at col. 10, lines 8-10.)

U.S. Pat. No. 7,635,380 (hereinafter "the '380 patent") describes a bone anchor compressor element for dynamic stabilization and motion preservation. The system 100 described in the '380 patent includes an anchor system 102, a horizontal rod system 104, and a vertical rod system 106. (The '380 patent at col. 7, lines 8-11.) The system 100 is connected to a spine via bone screws 108 with a head or saddle 110 that provides multiple degrees of freedom. (The '380 patent at col. 7, lines 15-29.)

U.S. Pat. No. 7,608,107 (hereinafter "the '107 patent") describes an expandable implant with interlocking walls and methods of use thereof. One embodiment is illustrated in FIGS. 24-29. There, the implant 400 includes an expanding and locking end cap 500. (The '107 patent at col. 19, lines 37-40.) The implant 400 includes an external thread 414 that permits the implant to be rotatably inserted into bone. (The '107 patent at col. 19, lines 53-62.) Additionally, bone screws 478 may be employed to secure the implant 400 in the bone. (The '107 patent at col. 20, lines 2-9.)

U.S. Pat. No. 7,066,960 (hereinafter "the '960 patent") describes an intervertebral disk replacement. The prosthetic implant 40 includes a matrix 41 with a substrate of bioincorporable continuous fabric. (The '960 patent at col. 7, lines 29-30.) As illustrated in FIGS. 6 and 7, biocompatible screws 69, 78 may be used to secure the implant in its intervertebral location. (The '960 patent at col. 10, lines 20-67.) As illustrated in FIG. 10A, one embodiment of the implant 100 includes a protrusion 106 that engages a mating slot formed in the vertebral body. (The '960 patent at col. 12, lines 25-30.)

U.S. Pat. No. 6,776,798 (hereinafter "the '798 patent") describes a spacer 12 for use in spinal surgeries, where the insert has an end cap 10 with a serrated surface. (The '798 patent at col. 4, lines 19-27.) The spacer 12 is inserted into the anterior portion 18 of a spine 14. (The '798 patent at col. 4, lines 22-24.) The end caps 10 are coupled to the ends 24, 26 of the spacer for use in interbody fusion surgeries. (The '798 patent at col. 4, lines 66-67.)

U.S. Pat. No. 6,132,430 (hereinafter "the '430 patent") describes a spinal fixation system. The spinal fixation system 10 includes a spinal rod 12 connected to vertebrae via bone screws 14. (The '430 patent at col. 5, lines 1-7.) The spinal rod 12 is external to the vertebrae 26, as illustrated in FIG. 2.

U.S. Pat. No. 5,928,232 (hereinafter "the '232 patent") describes a spinal fixation system that connects externally to spinal vertebrae, as depicted in FIG. 1. The system is implantable to surgically correct spinal disorders. (The '232 patent at col. 1, lines 10-14.)

U.S. Pat. No. 5,776,134 (hereinafter "the '134 patent") describes a low-profile spinal fixation system. As illustrated in FIG. 2, the system is connectible to the exterior of a spine to correct specific disorders such as scoliosis. (The '134 patent at col. 1, lines 18-22.)

Each of these prior art examples describe different devices that are designed to address specific spinal disorders and ailments.

These devices, however, do not permit a surgeon to secure an intervertebral spacer while also applying a predetermined amount of compression. Other deficiencies in the prior art also should be apparent to those skilled in the art.

SUMMARY OF THE INVENTION

The present invention addresses one or more of the deficiencies noted above with respect to the related art.

In one embodiment, the present invention provides a vertebral spacer that includes a body with a top side, a bottom side, a front side, and a rear side. The top side is configured to be positioned adjacent to a first vertebra and the bottom side is configured to be positioned against a second vertebra. A first bore extends from a first opening in the front side to a second opening on the top side, a second bore extends from a third opening in the front side to a fourth opening on the top side, a third bore extends from a fifth opening on the front side to a sixth opening on the bottom side, and a fourth bore extends from a seventh opening on the front side to an eighth opening on the bottom side. First and second compression fasteners are disposable in the first and third bores, and first and second locking fasteners are disposable in the second and fourth bores. The first compression fastener and the first locking fastener cooperate to apply and lock a first predetermined compression force between the body and the first vertebra. The second compression fastener and the second locking fastener cooperate to apply and lock a second predetermined compression force between the body and the second vertebra.

It is contemplated that the top side and the bottom side of the body may be substantially parallel to one another.

Alternatively, it is contemplated that at least one of the top side or the bottom side are disposed at a first angle of between about 10° to 20° from horizontal.

Still further, it is contemplated that the first angle may be about 15° from horizontal.

The vertebral spacer of the present invention may be constructed such that at least one of the first bore, the second bore, the third bore, and the fourth bore are disposed at a second angle of between about 40° to 65° from horizontal. If so, the second angle may be between about 40° to 50° from horizontal. Alternatively, the second angle may be about 45°. In another contemplated embodiment, the second angle may be between about 55° to 65° from horizontal, with a specific second angle being about 60°.

It is contemplated that the vertebral spacer of the present invention may have the first opening, the third opening, the fifth opening, and the seventh opening disposed along a line on the front side of the body.

It is also contemplated that the first opening, the third opening, the fifth opening, and the seventh opening are not disposed along a line on the front side of the body.

In one embodiment, each compression fastener may include a shaft and threads disposed along a portion of the shaft, wherein the threads are bone-engaging threads that are engageable with the first or second vertebra.

Each locking fastener may include a shaft and threads disposed therealong, wherein a portion of the threads are bone-engaging threads and a portion of the threads are body-engaging threads, the bone-engaging threads are engageable with the first or second vertebra, and the body-engaging threads are engageable with the body.

In a further embodiment, the vertebral spacer may include a fifth bore extending from a ninth opening in the front side to a tenth opening on the top side and a sixth bore extending from an eleventh opening on the front side to a twelfth opening on the bottom side.

In this contemplated embodiment, compression fasteners may be disposable in the fifth and sixth bores. Alternatively, locking fasteners may be disposable in the fifth and sixth bores.

In an additional contemplated embodiment of the vertebral spacer of the present invention, at least one protrusion may be disposed on at least one of the top side or the bottom side, the at least one protrusion being engageable with at least one of the first and second vertebrae. Alternatively, the protrusion may be a plurality of protrusions. Further still, the plurality of protrusions may be disposed at corners of the body.

In another embodiment, it is contemplated that the vertebral spacer may includes at least one recess in register with at least one of the bores to accommodate a head on at least one of the locking fastener and the compression fastener.

In a further contemplated embodiment, the vertebral spacer may include a face plate disposed on the body, at the front side. If so, the face plate is contemplated to define the first, third, fifth, and seventh openings.

If included, the face plate may be integrally molded with the body.

If incorporated into the vertebral spacer, the face plate may be made from a metal or metal alloy suitable for placement in a living organism.

It is contemplated that, where a face plate is incorporated into the vertebral spacer, the face plate will define a lip surrounding each of the first, third, fifth, and seventh openings.

Where the face plate includes a lip around the openings therein, the compression fasteners are contemplated to include a threaded portion and a non-threaded portion, the non-threaded portion being adjacent to a head thereof, the head engaging a respective lip to apply compression force between the body and an adjacent vertebra.

Where the faceplate includes a lip portion around openings therein, the locking fasteners are contemplated to include a threaded portion adjacent to a head thereof, the threaded portion engaging a respective lip to apply a locking force between the body and an adjacent vertebra.

Additional advantages of the present invention should be appreciated by those skilled in the art from the discussion that follows.

BRIEF DESCRIPTION OF THE DRAWINGS

Various embodiments of the present invention are described in connection with the drawings appended hereto, in which.

DESCRIPTION OF EMBODIMENT(S) OF THE INVENTION

The present invention will now be described in connection with one or more embodiments thereof. Discussion of specific embodiments is intended to be illustrative of the breadth and scope of the present invention. In other words, discussion of specific embodiments is not intended to be limiting of the present invention. Those skilled in the art are likely to appreciate many variations and equivalents that are suggested by the embodiments described in the present invention. Those variations and equivalents are intended to be encompassed by the present invention.

As a preliminary matter, the embodiments of the spacer of the present invention are intended for use in spinal surgeries on human beings. While the present invention is described in this context, the present invention may be applied to any other vertebrate without departing from the scope of the present invention.

Next, the spacer of the present invention is intended to be inserted from a posterior spinal location. While a posterior insertion is considered the most likely insertion orientation, the present invention may be inserted between vertebrae from any spinal position, without departing from the scope thereof.

Various aspects of the present invention may be described in connection with one or more embodiments of the present invention. The discussion of a specific feature in connection with one embodiment should not be understood to infer that the feature is associated solely with that embodiment. To the contrary, as should be apparent to those skilled in the art, features described in connection with one embodiment of the present invention may be employed in connection with other embodiments without departing from the scope of the present invention.

Figure 1:
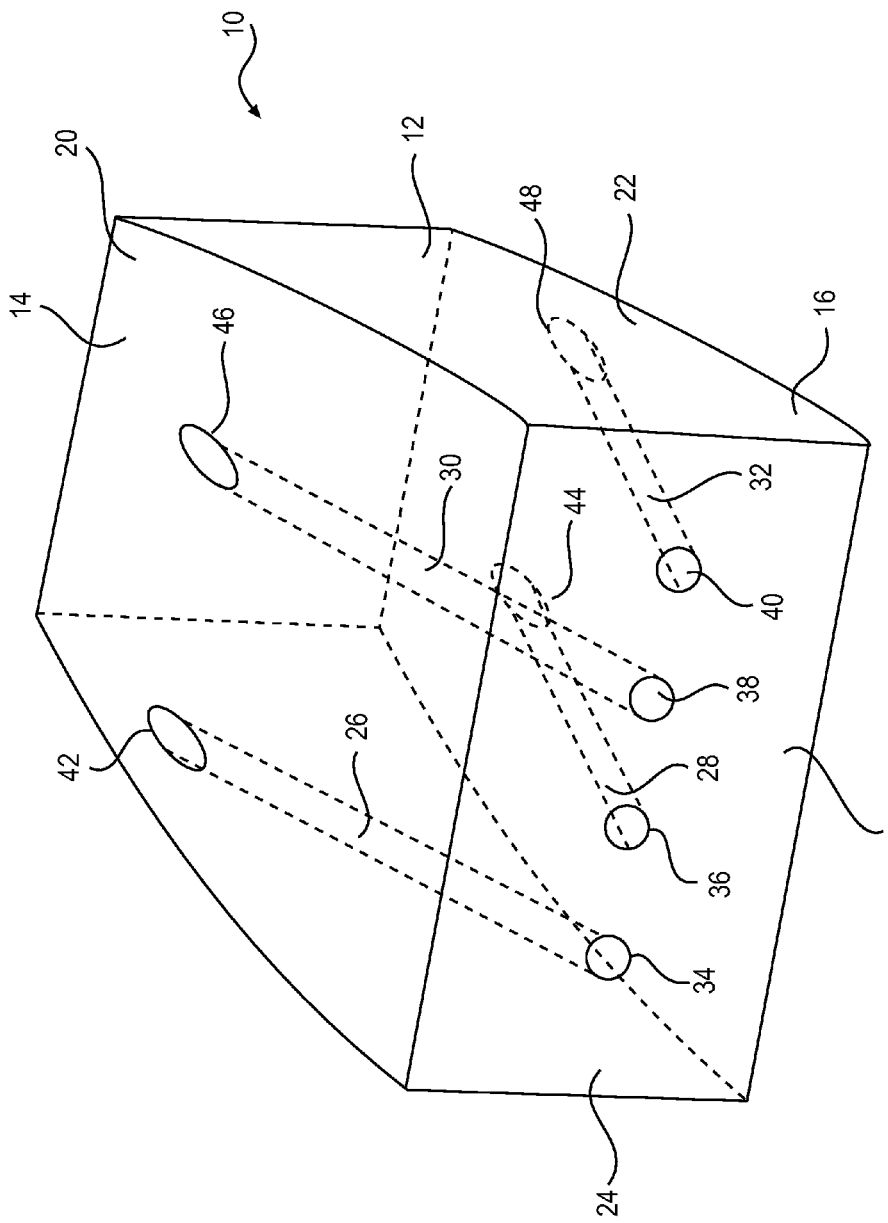
FIG. 1 is a perspective illustration of a first embodiment of the spacer of the present invention.

FIG. 1 illustrates a first embodiment of the spacer 10 of the present invention. The spacer 10 is illustrated as a block or body 12 with a top side 14, a bottom side 16, a front side 18, a rear side 20, a right side 22 and a left side 24. In other words, the spacer 10 is essentially a polygonal, six-sided structure, at least in this first contemplated embodiment.

It is contemplated that the spacer 10 may take any suitable shape, as should be apparent to those skilled in the art. For example, it is contemplated that the spacer 10 may be circular, ellipsoidal, polygonal, or amorphously shaped. Moreover, it is contemplated that the spacer 10 may have an initial shape that may be adjusted by a surgeon to facilitate placement of the spacer between two adjacent vertebrae. For example, if a spacer's shape needs to be changed to accommodate a patient's individual anatomy, the spacer may be made from a material that permits the surgeon to carve away portions of the spacer. Alternatively, the spacer may be constructed from a material that permits the surgeon to melt and sculpt the spacer.

As described in greater detail below, the spacer 10 is intended for insertion, posteriorly, between adjacent vertebrae in a spinal column. The spacer 10, therefore, may be used for a number of appreciable purposes. For example, the spacer 10 may be employed to replace, wholly or in part, a damaged cartilage disc in a person's spinal column. In an alternative contemplated use, the spacer 10 may be used to fix (or fuse) adjacent vertebrae to one another. Still further uses may be contemplated by those skilled in the art. Accordingly, an exhaustive list is not provided herein.

In the discussion that follows, the spacer 10 of the present invention is described in the context of use as a device to assist with the fusion of adjacent vertebrae to one another. While the following discussion focuses on this particular use, the present invention is not intended to be limited thereby. To the contrary, the present invention may be used for any purpose without departing from the scope discussed herein.

The spacer 10 is illustrated in FIG. 1 as a modified cubical structure. As illustrated, the front side 18, the rear side 20, the top side 14, and the bottom side 16 are planar in shape. The right side 22 and the left side 24 are both curved.

While the shape illustrated in FIG. 1 represents one particular shape contemplated for the spacer 10, the spacer 10 may take any shape without departing from the scope of present invention. In other words, the spacer 10 may be fashioned into any shape as may be appropriate for the specific use contemplated for the spacer 10.

The body 12 of the spacer 10 may be made from any suitable material. For example, the spacer 10 may be made from materials including metals (such as stainless steel or titanium), alloys, plastics, thermoplastics, polymers, ceramics, composite materials, and any combination of these materials. While the exact composition of the spacer 10 is not critical to practice of the present invention, the present invention is intended for implantation into the human body. As a result, the spacer 10 of the present invention is anticipated to be made from one or more materials that are compatible with human biology.

Additionally, it is contemplated that the spacer 10 may be constructed from one or more materials that are at least partially elastic. In the context of the use of the spacer 10 as an apparatus to fuse adjacent vertebrae to one another, a predetermined amount of elasticity may be desirable to permit some flexure between the vertebrae connected by the spacer 10 of the present invention. Alternatively, it is contemplated that the spacer 10 may be made from an inelastic material to discourage relative motion between the vertebrae connected thereto.

It is contemplated that the spacer 10 of the present invention will be connected to adjacent vertebrae 10 using fasteners, such as screws, for example. As should be apparent to those skilled in the art, other fasteners may be substituted therefor without departing from the scope of the present invention. One or more contemplated modes of connection are described in greater detail below.

In the embodiment illustrated in FIG. 1, the spacer 10 includes four bores 26, 28, 30, 32. The four bores also are referred to herein as the first bore 26, the second bore 28, the third bore 30, and the fourth bore 32. The bores 26, 28, 30, 32 extend from first openings 34, 36, 38, 40 to second openings 42, 44, 46, 48. The bores 26, 28, 30, 32 are illustrated as cylindrical holes that extend between the first openings 34, 36, 38, 40 to the second openings 42, 44, 46, 48.

With respect to the shapes of the bores 26, 28, 30, 32, it is contemplated that they will be cylindrical, as illustrated. However, the bores 26, 28, 30, 32 may have any cross-sectional shape without departing from the scope of the present invention.

As illustrated in FIG. 1, the first bore 26 extends from the first opening 34 to the second opening 34. The first opening 34 is illustrated as an opening on the front side 18 of the spacer 10. The second opening 42 is located on the top side 14 of the spacer 10. The second bore 28 extends from the first opening 36 to the second opening 44. The first opening 36 also is positioned on the front side 18 of the spacer 10. The second opening 44, however, is on the bottom surface 16 of the spacer 10. The third bore 30 extends between the first opening 38 and the second opening 46. The first opening 38 is located on the front side 14. The second opening 46 is located on the top side 14 of the spacer 10. The fourth bore 32 extends between the first opening 40 and the second opening 48. The first opening 40 is located on the front side 18 and the second opening is located on the bottom side 16.

The four bores 26, 28, 30, 32 are disposed in the spacer 10 such that fasteners may be inserted therein, thereby permitting the spacer 10 to be connected to adjacent vertebrae in a spinal column.

Figure 2:
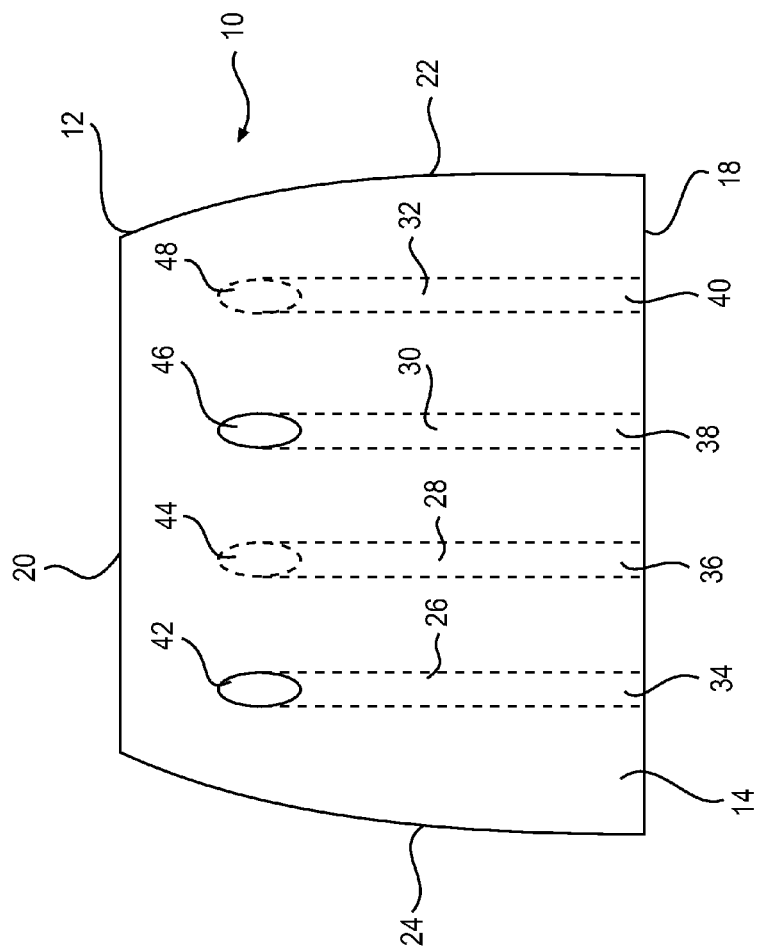
FIG. 2 is a top view illustration of the spacer shown in FIG. 1.

FIG. 2 is a top view of the spacer 10 illustrated in FIG. 1. The curved shapes of the right side 22 and the left side 24 are more readily appreciated from this drawing.

FIG. 2 also illustrates the relative positioning between the bores 26, 28, 30, 32. As illustrated, the bores 26, 28, 30, 32 are parallel to one another. In addition, the bores 26, 28, 30, 32 are illustrated with equal lengths. In one contemplated alternative, it is contemplated that the bores 26, 28, 30, 32 are not parallel to one another. In another contemplated embodiment, the bores 26, 28, 30, 32 are not of equal lengths. Still other configurations are contemplated for the spacer 10 of the present invention. Those other configurations may be employed without departing from the scope of the present invention.

In one contemplated embodiment, the bores 26, 32 may be angled toward a centerline of the spacer 10 at an angle of 25° to 35°, with a preferred angle of about 30°. In this embodiment, the bores 28, 30 are contemplated to be angled with respect to a centerline of the spacer 10 by 10° to 20°, with 15° degrees being preferred.

Figure 3:
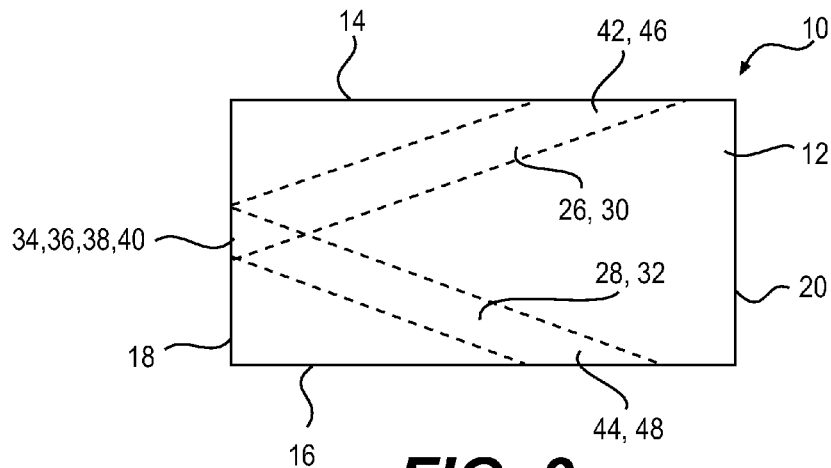
FIG. 3 is a side view illustration of the spacer shown in FIG. 1.

FIG. 3 is a side view of the spacer 10 of the present invention. The rectangular profile of the spacer 10 is evident in this illustration. In addition, the relative positioning of the bores 26, 28, 30, 32 with respect to one another also is visible. As described above in connection with FIG. 1, the bores 26, 30 extend from the front side 18 to the top side 14 of the spacer 10. The bores 28, 32, on the other hand, extend from the front side 18 to the bottom side 16 of the spacer 10.

Figure 4:
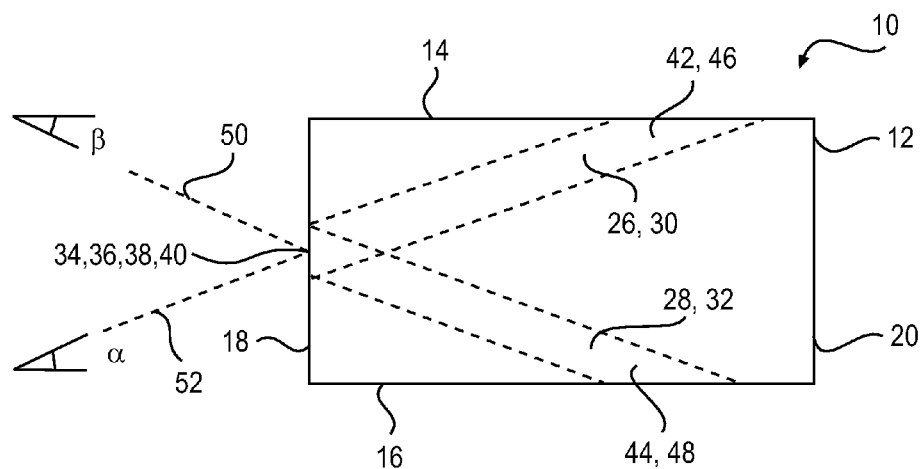
FIG. 4 is a side view illustration of the spacer shown in FIG. 1, indicating the angular orientations of bores in the spacer.

FIG. 4 provides a second side view of the spacer 10 of the present invention. This view is the same as that provided in FIG. 3. In FIG. 4, the axes 50 of the bores 26, 30 are illustrated. The axes 52 for the bores 28, 32 also are indicated. The axis 50 is disposed at an angle β from horizontal. The axis 52 is disposed at an angle α from horizontal. In the embodiment illustrated in FIG. 4, α=β. However, the present invention contemplates embodiments where α≤β. Alternatively, the present invention also contemplated that α≥β.

For the spacer 10 of the present invention, the angles α, β preferably are between 40° to 65°, inclusive. An angle of 45° is perhaps the most preferred angle α, β. Accordingly, a range of angles of 40° to 50° is anticipated to be the most commonly employed embodiment. Where an angle α, β of 60° is employed, the angle α, β may be in a range between 55° to 65°, for example.

Figure 5:
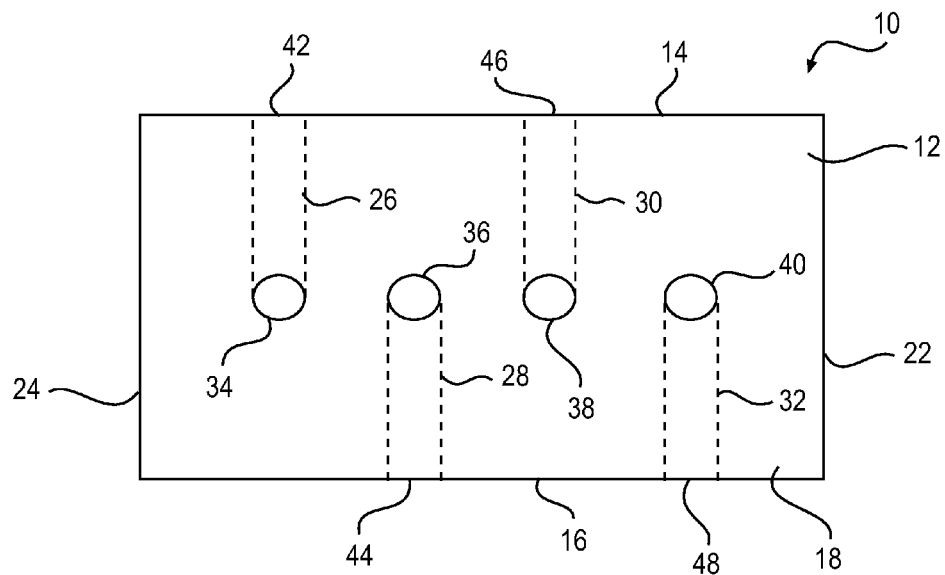
FIG. 5 is a front view illustration of the spacer shown in FIG. 1.

FIG. 5 is a front view of the spacer 10 of the present invention. The positions of the bores 26, 28, 30, 32 are shown. As discussed previously, the first bore 26 extends from the front side 18 to the top side 14. The second bore 28 extends from the front side 18 to the bottom side 16 of the spacer 10. Like the first bore 26, the third bore 30 extends from the front side 18 to the top side 14 of the spacer 10. Similarly, like the second bore 28, the fourth bore 32 extends from the front side 18 to the bottom side 16 of the spacer 10.

In the embodiment of the spacer 10 of the present invention illustrated in FIGS. 1-5, the first and third bores 26, 30 extend upwardly from the front side 18 to the top side 14 of the spacer 10. The second and fourth bores 28, 32 extend from the front side 18 to the bottom side 16 of the spacer 10. While this arrangement is contemplated for one embodiment of the present invention, it is also contemplated that the bores 26, 28, 30, 32 may be provided in a different configuration.

Figure 6:
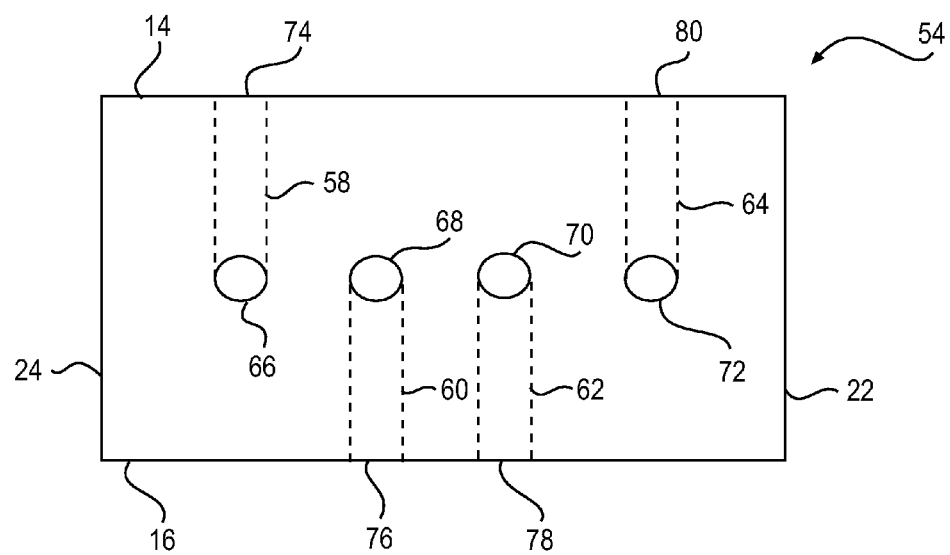
FIG. 6 is a front view illustration of a second embodiment of the spacer of the present invention.

FIG. 6 is a front view of a second embodiment of the spacer 54 of the present invention. In this embodiment, the spacer 54 includes a body 56 with four bores 58, 60, 62, 64. As a point of reference, the top side 14, bottom side 16, right side 22, and left side 24 are provided with the same reference numerals as the first embodiment of the spacer 10.

As shown in FIG. 6, the first bore 58 extends from a first opening 66 in the front side 18 to a second opening 74 on the top side 14. The second bore 60 extends from a first opening 68 in the front side 18 to a second opening 76 in the bottom side 16 of the spacer 54. The third bore 62 extends from a first opening 70 in the front side 18 to a second opening 78 in the bottom side 16 of the spacer 54. The fourth bore 64 extends from a first opening 72 in the front side 18 to a second opening 80 in the top side 14 of the spacer 54.

A comparison between FIG. 5 and FIG. 6 illustrates the apparent differences between these two embodiments. In the first embodiment of the spacer 10, the first and third bores 26, 30 extend to the top side 14 of the spacer 10. In the second embodiment of the spacer 54, the first and fourth bores 58, 64 extend to the top side 14 of the spacer 54.

These two embodiments of the spacers 10, 54 of the present invention indicate still further embodiments contemplated for the present invention. For example, with reference to the first embodiment of the spacer 10, the bores 26, 30 could be oriented to extend to the bottom side 16 of the spacer 10 rather than the top side 14. If so, the bores 28, 32 could be oriented to extend to the top side 14 rather than the bottom side 16 of the spacer 10. Similarly, with reference to the spacer 54, the bores 58, 64 could extend from the front side 18 to the bottom side 16 of the spacer 54. In addition, the bores 60, 62 could extend from the front side 18 to the top side 14 of the spacer 54.

In each of the first and second embodiments of the spacers 10, 54, the bores extend perpendicularly to the front side 18 and the rear side 20. In addition, the bores extend substantially parallel to the right side 22 and the left side 24 of the spacers 10, 54. The orientation of the bores, however, may be altered from these illustrated embodiments without departing from the scope of the present invention.

Figure 7:
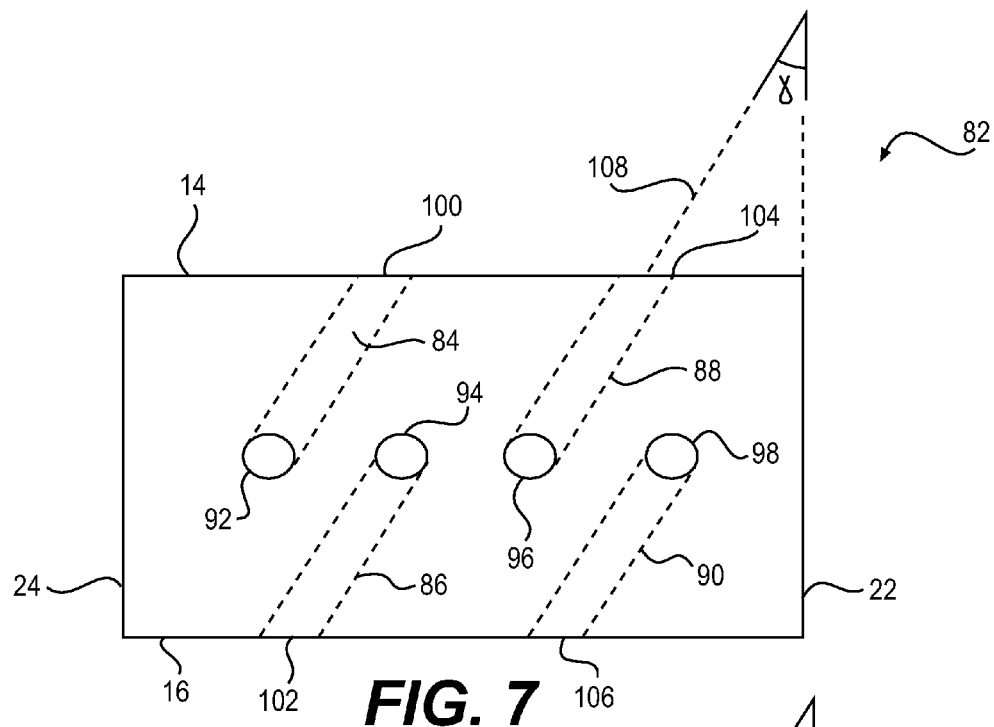
FIG. 7 is a front view illustration of a third embodiment of third embodiment of the spacer of the present invention.

FIG. 7 is a front view of a third embodiment of a spacer 82 according with the present invention. As with the prior embodiments, reference numerals for the top side 14, the bottom side 16, the right side 22, and the left side 24 are retained for this third embodiment.

The spacer 82 includes four bores 84, 86, 88, 90. The bores 84, 86, 88, 90 extend from first openings 92, 94, 96, 98 to second openings 100, 102, 104, 106. As with the first embodiment of the spacer 10, the bores 84, 86, 88, 90 alternately extend to the top sides 14 and the bottom sides 16 of the spacer 82. This embodiment differs from the prior two embodiments in that the bores 84, 86, 88, 90 have axes 108 that are angled, at angle γ, with respect to planes defined by the right side 22 of the spacer 82. As should be apparent to those skilled in the art, the bores 84, 86, 88, 90 need not have the same angles, as illustrated.

Figure 8:
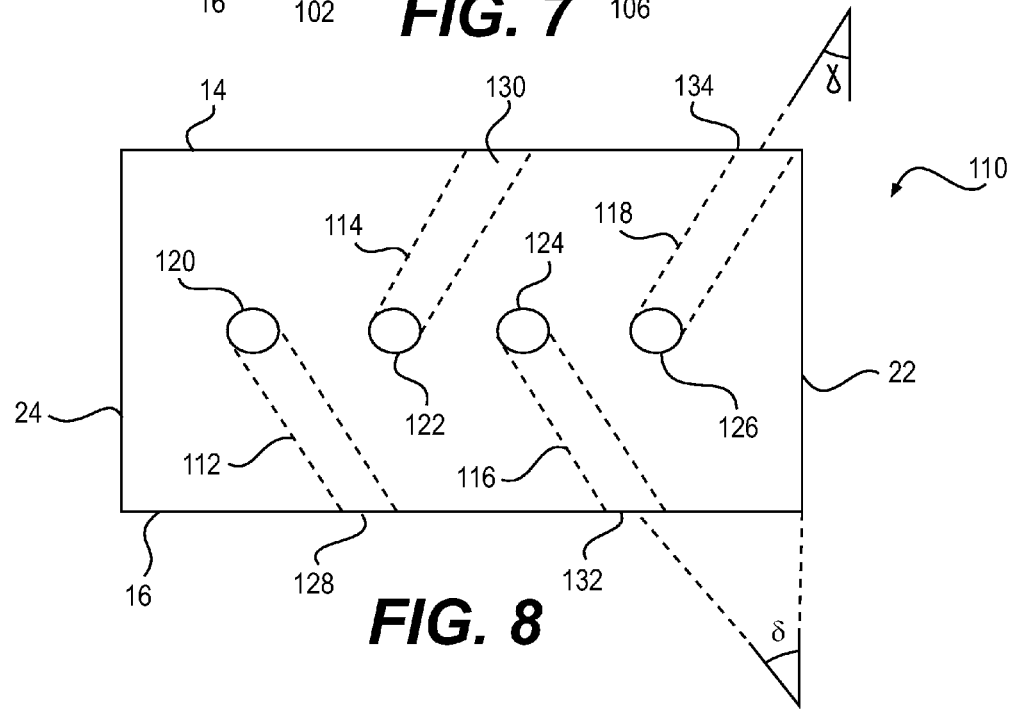
FIG. 8 is a front view illustration of a fourth embodiment of the spacer of the present invention.

FIG. 8 is a front view of a fourth embodiment of a spacer 110. Here, the bores 112, 114, 116, 118 extend from first openings 120, 122, 124, 126 to second openings 128, 130, 132, 134. The bores 112, 114, 116, 118 are disposed at angles γ, δ with respect to the right side 22 of the spacer 110. The angles γ, δ are contemplated to be between 10° to 35°, with 15° and 30° being preferred.

Figure 9:
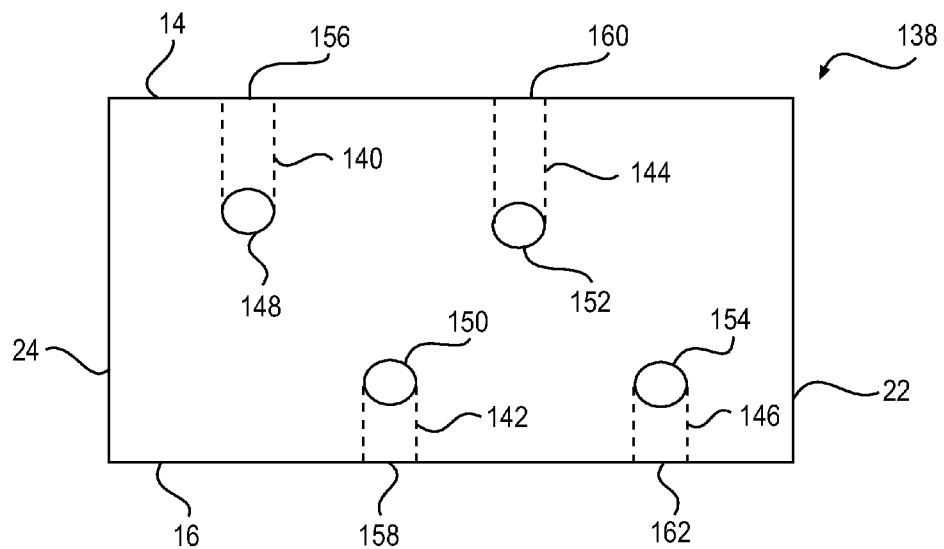
FIG. 9 is a front view illustration of a fifth embodiment of the spacer of the present invention.

FIG. 9 is a front view of a fifth embodiment of a spacer 138 according to the present invention. This spacer 138 also includes four bores 140, 142, 144, 146 that extend from first openings 148, 150, 152, 154 to second openings 156, 158, 160, 162. This embodiment differs from prior embodiments in that the first openings 148, 150, 152, 154 are not in line with one another.

Figure 10:
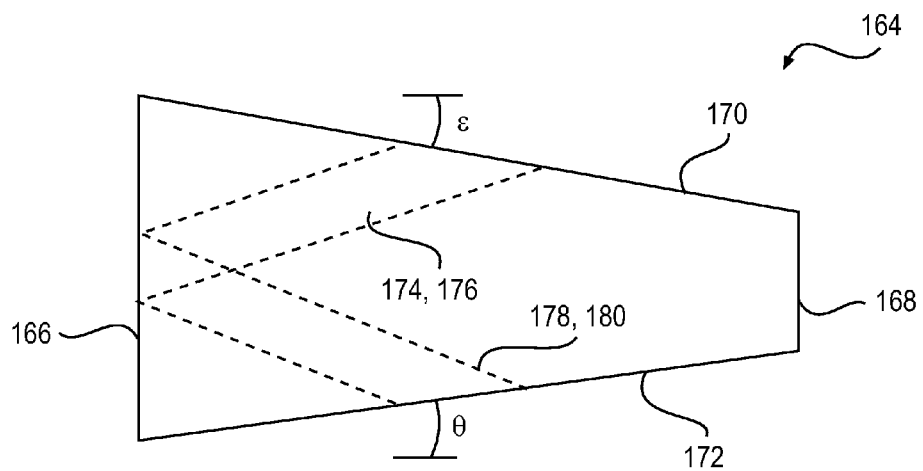
FIG. 10 is a side view illustration of a sixth embodiment of the spacer of the present invention.

FIG. 10 is a side view of a sixth embodiment of a spacer 164 according to the present invention. In this embodiment, the front side 166 is parallel to the rear side 168, as in prior embodiments. The top side 170 and the bottom side 172, however, are not parallel. Specifically, the top side 170 is angled, at angle E, to the horizontal. The bottom side 172 is angled, at angle θ, from the horizontal. As a result, the spacer 164 has a wedge shape. This spacer 164 also is intended to include bores 174, 176, 180, 182. The bores 176, 178, 180, 182 extend from the front side 16 to the top and bottom sides 170, 172 in any of the configurations previously described, for example. In this embodiment, the angles ε, θ fall between 10° and 20°, with 15° being preferred.

Figure 11:
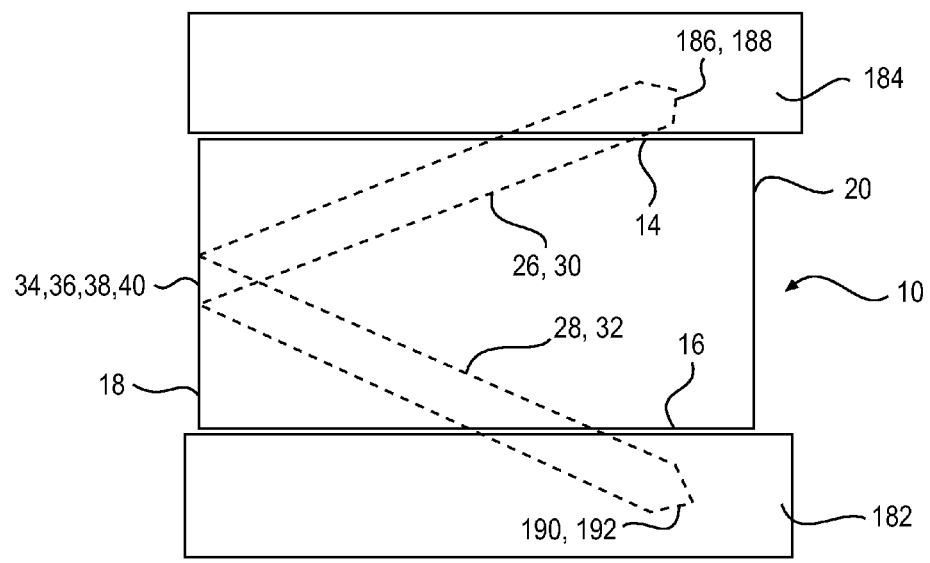
FIG. 11 is a side view illustration of the placement of the first embodiment of the spacer of the present invention between two adjacent vertebrae, the drawing depicting bores in the vertebrae that are in register with the bores in the spacer.

FIG. 11 is a side view illustration of the spacer 10 of the present invention. In this illustration, the spacer 10 is shown positioned between two vertebrae 182, 184. As shown in this illustration, the bores 26, 28, 30, 32 are in register with bores 186, 188, 190, 192 in the vertebrae 182, 184. This permits fasteners, which are described in greater detail below, to be inserted into the bores 26, 28, 30, 32, 186, 188, 190, 192.

Figure 12:
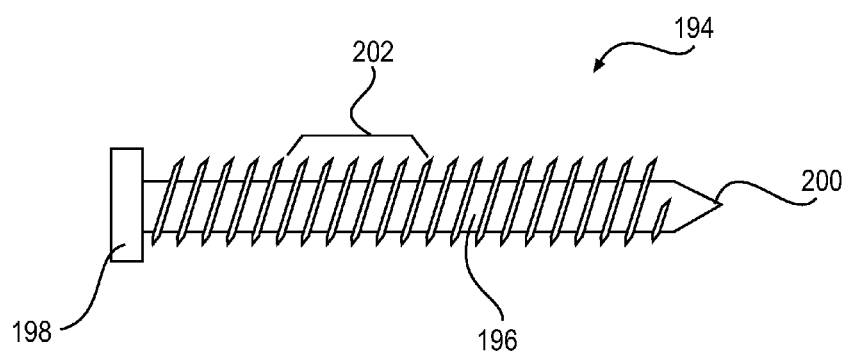
FIG. 12 is a side view illustration of a locking fastener to be used in connection with the spacer of the present invention.

FIG. 12 is a side view illustration of a locking fastener 194 in accordance with the present invention. The locking fastener 194 is a screw with a shaft 196, a head 198, a tip 200 and a plurality of threads 202 disposed along the shaft 196. The locking fastener 194 is anticipated to be made from a suitable metal such as stainless steel or titanium. However, as should be appreciated by those skilled in the art, the locking fastener 194 may be made from any material suitable for implantation in a human being or other animal.

With reference to the head 198 of the locking fastener 194, the head 198 may be provided with any suitable engaging surface such that the locking fastener 194 may be manipulated by a tool with a Phillips head engagement, a flat head engagement, an Allen wrench engagement, or the like.

As illustrated in FIG. 12, the locking fastener 194 includes threads 202 along the entire length of the shaft 196. This permits the locking fastener 194 to engage a vertebra 182, 184 and also to engage the spacer 10, 54, 82, 110, 138, 164.

Figure 13:
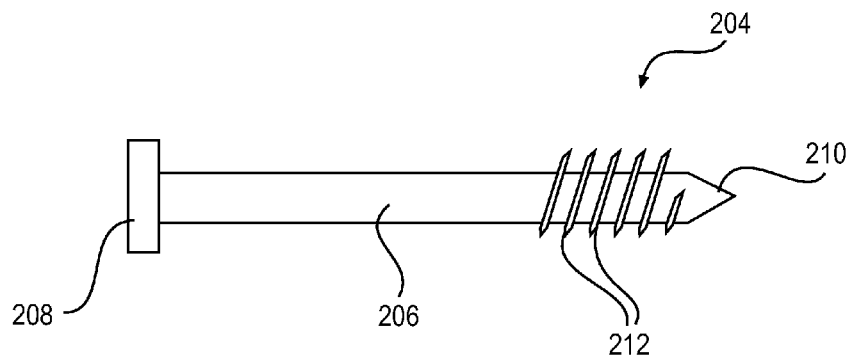
FIG. 13 is a side view of a compression fastener to be used in connection with the spacer of the present invention.

FIG. 13 is a side view of a compression fastener 204. The compression fastener 204 includes a shaft 206, a head 208, a tip 210, and threads 212. As with the locking fastener 194, the compression fastener 204 is contemplated to be made from a metal such as stainless steel or titanium. However, any alternative material suitable for implantation in a body may be employed without departing from the scope of the present invention.

As with the locking fastener 194, the head 208 of the compression fastener 204 may be provided with any suitable engaging surface such that the locking fastener 204 may be manipulated by a tool with a Phillips head engagement, a flat head engagement, an Allen wrench engagement or the like.

As illustrated in FIG. 13, the compression fastener 204 includes threads 212 along only a portion of the shaft 206. This permits the threads 212 of the compression fastener 204 to engage a vertebra 182, 184 without also engaging the spacer 10, 54, 82, 110, 138, 164.

Figure 14:
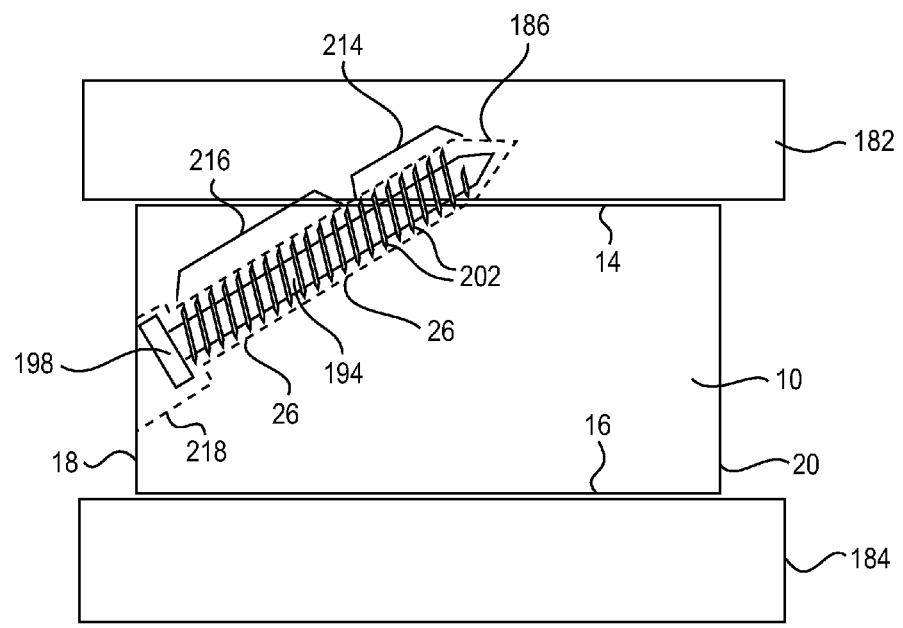
FIG. 14 is a side view illustration of the spacer of the present invention shown in FIG. 1, further depicting the positioning of a locking fastener therein.

FIG. 14 is a side view of the relative positioning of the spacer 10 between two vertebrae 182, 184. In this illustration, a locking fastener 194 is shown, having been inserted into the bore 26 in the spacer 10. A portion of the threads 202 on the locking fastener 194 engage the interior surface of the bore 186 in the vertebra 182. The threads 202 that engage the interior of the bore 186 are referred to as the bone-engaging threads 214 for purposes of the discussion that follows. As is apparent from the drawing, the remaining threads 202 engage the interior of the bore 26 in the spacer 10. These threads 202 are referred to as spacer-engaging threads 216 for purposes of the discussion that follows.

FIG. 14 also illustrates a feature of the spacer 10 that may be provided. Specifically, the spacer includes a recess 218 to accommodate the head 198 of the locking fastener 194. The recess 218 is not critical to operation of the present invention. It is illustrated in FIG. 14 as an alternative embodiment. As should be apparent, the recess 218 permits the head 198 to be sunk below the plane defined by the front side 18 of the spacer 10.

Figure 15:
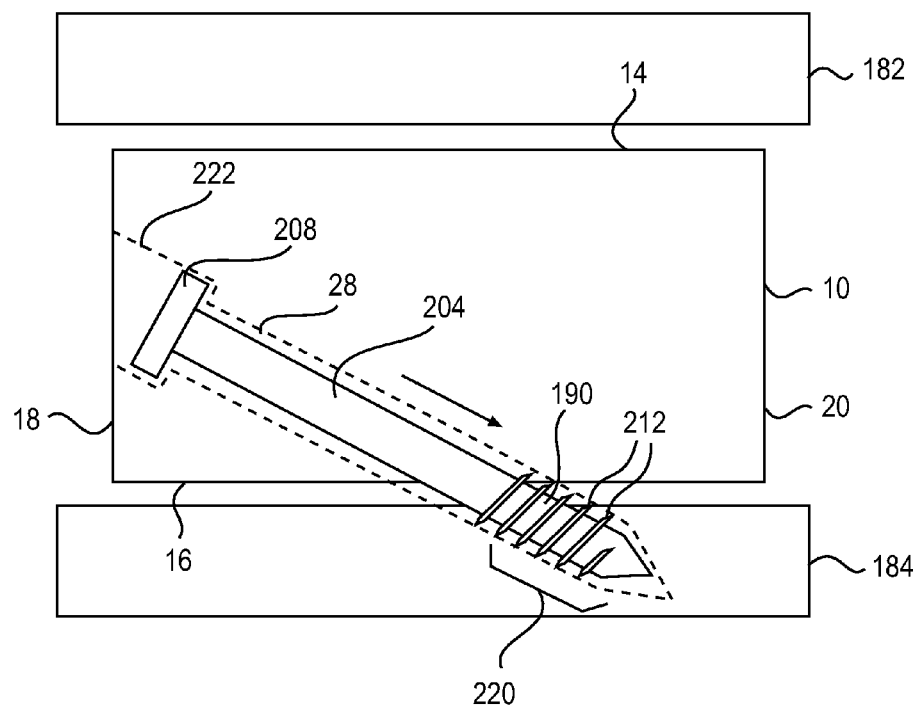
FIG. 15 is a side view illustration of the spacer of the present invention shown in FIG. 1, further depicting the positioning of a compression fastener therein.

FIG. 15 also is a side view illustration of the relative positioning of the spacer 10 between two vertebrae 182, 184. In this drawing, however, a compression fastener 204 is illustrated in the bore 28, 190. As shown, the threads 212 extend along the shaft 206 only at the location where the compression fastener 204 engages the interior of the bore 190 within the vertebra 184. Consistent with the discussion of the locking fastener 194, the threads 212 that engage the vertebra 184 also are designated as bone-engaging threads 220. For the compression fastener 204, there are no spacer-engaging threads.

It is noted that the spacer 10 also includes a recess 222 to accommodate the head 208 of the compression fastener 204.

Figure 16:
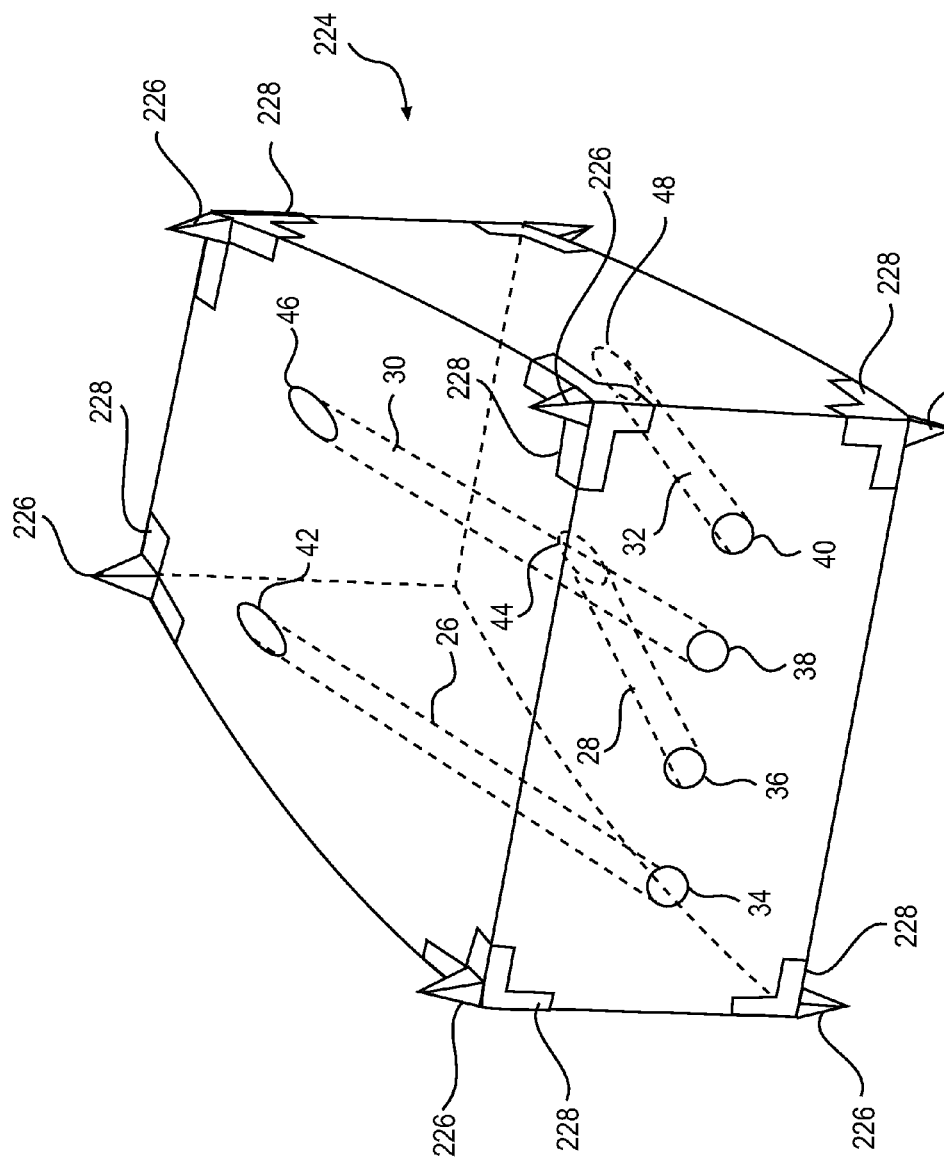
FIG. 16 is a perspective illustration of a seventh embodiment of a spacer according to the present invention.
Figure 17:
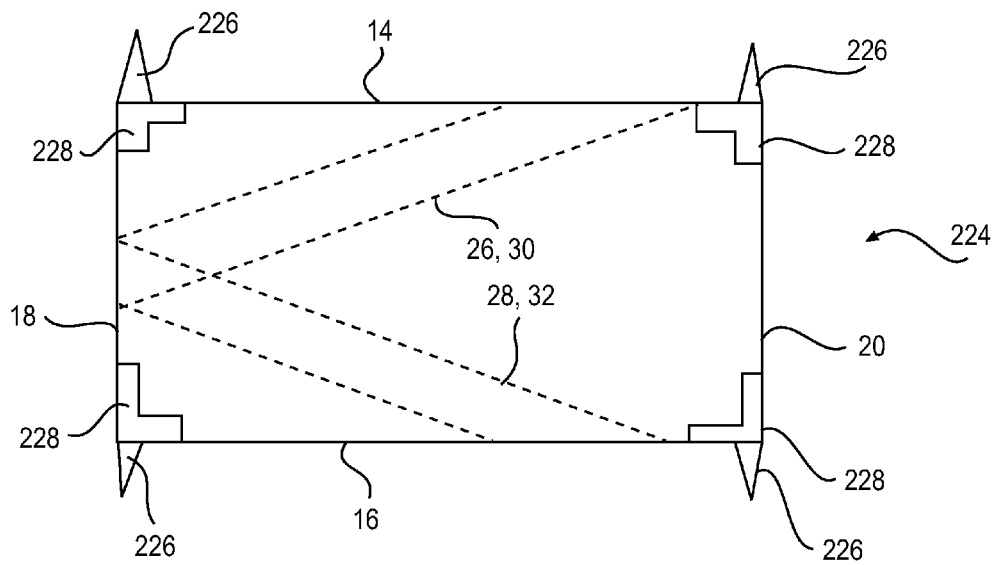
FIG. 17 is a side view illustration of the spacer shown in FIG. 16.

FIG. 16 is a perspective illustration of a spacer 224 according to a seventh embodiment of the present invention. The spacer 224 identical to the spacer 10, except that the spacer 224 is provided with a plurality of protrusions 226 at each of the corners thereof. The protrusions 226 are intended to provide increased positional stability for the spacer 224 by comparison with the spacer 10 that does not include the protrusions 226.

The protrusions 206 are contemplated to be made from metal, such as stainless steel or titanium. As noted above, however, any other material suitable for implantation into a living organism is considered to fall within the scope of the present invention.

In the illustrated embodiment, the protrusions 206 are provided at the corners of the spacer 224. So that the protrusions are adequately secured at these locations, they are connected to corner supports 228 that are connected to the spacer 224.

As should be apparent to those skilled in the art, the protrusions 206 may be positioned at any location on the top side 14 and the bottom side 16 of the spacer 224. Moreover, the protrusions need not be made from a material different from the material that comprises the spacer 224. It is contemplated that the protrusions 226 may be integrally formed with the spacer 224, at least in one contemplated variation.

While the protrusions 206 are contemplated to be provided on the top side 14 and the bottom side 16 of the spacer 224, specific requirements for the spacer 224 may dictate that the protrusions 226 be excluded from one of the sides. Additionally, it is contemplated that one or more protrusions 206 may be provided on any of the remaining sides of the spacer 224 without departing from the scope of the present invention.

Renewed reference is now made to FIGS. 1, 14, and 15. These figures provide a basis to discuss the cooperative effect between the spacer 10, the locking fasteners 194 and the compression fasteners 204.

As noted above, prior art vertebral spacers typically apply only a locking force to two adjacent vertebrae. However, to establish a more effective connection between adjacent vertebrae, a compressive force is desirable. The present invention addresses this deficiency (among others) in the prior art.

As illustrated in FIG. 1, the bores 26, 28, 30, 32 in the spacer are provided in pairs. This design feature is intentional.

The bores are intended to work in pairs with their associated fasteners 194, 204. Specifically, for each pair of bores, one bore is intended to accommodate one locking fastener 194 and the other bore is intended to accommodate one compression fastener 204. With respect to each pair of bores, therefore, the bore accommodating the compression fastener 204 provides a vehicle by which a compressive force may be applied between the spacer 10 and the adjacent vertebra 182, 184. The bore accommodating the locking fastener 194 provides a vehicle by which a locking force may be applied between the spacer 10 and the adjacent vertebra 182, 184.

As should be apparent from FIG. 15, when the compression fastener 204 is inserted into the bore, the bone-engaging threads 220 engage the interior of the bore 190 in the vertebra 184. Since the portion of the shaft 206 within the bore 28 does not include any threads, as the bone-engaging threads 220 pull the compression fastener 204 further into the vertebra 184, the spacer 10 is pulled more tightly against the vertebra 184 by interaction between the head 208 of the compression fastener 204 and the spacer 10. In other words, the head 208 applies pressure to the spacer 10 to push the spacer against the vertebra 184.

Once an appropriate compressive force is established between the spacer 10 and the vertebra 184, a locking fastener 194 is inserted into the complimentary bore. Since the locking fastener 194 includes threads 202 along the entirety (or nearly the entirety) of its shaft 196, the threads 202 engage both the interior surface of the bore in the spacer 10 and the interior surface of the bore in the vertebra 184. As a result, the locking fastener 194 presents an arrangement whereby the locking fastener 194 essentially prevents the spacer from altering its position relative thereto, once the locking fastener 194 is secured in place.

FIG. 14 illustrates the locking fastener 194 after being positioned in the vertebra 182. As illustrated, the bone engaging threads 214 engage the bore 186 in the vertebra 182. The spacer-engaging threads 216 engage the interior surface of the bore 26 in the spacer 10. The combination of the engagement of the vertebra 182 and the spacer 10 by the threads 202 of the locking fastener 194 establishes a stable locking between the vertebra 182 and the spacer 10.

Figure 18:
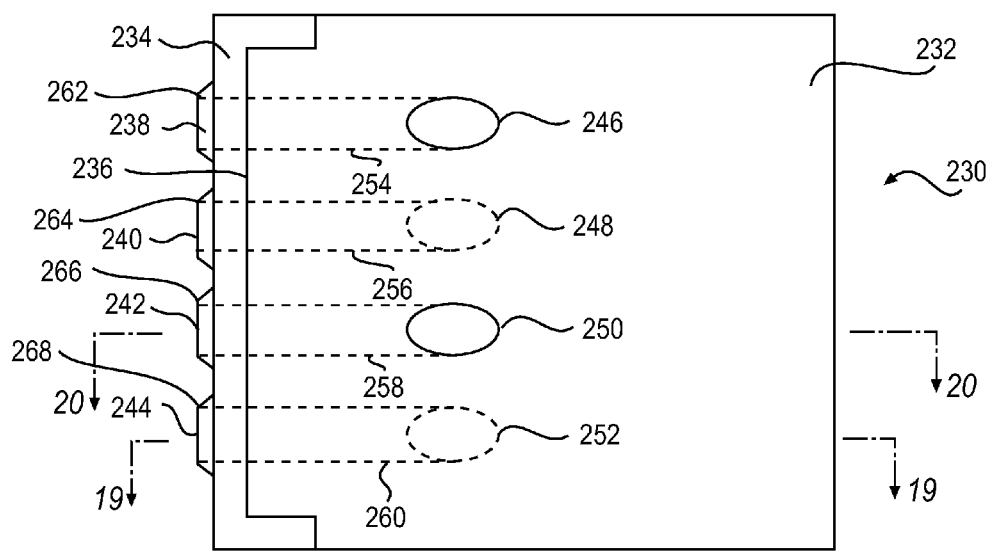
FIG. 18 is a top view of an eighth embodiment of the spacer of the present invention.

FIG. 18 provides a top view of a further embodiment of a spacer 230 according to the present invention. The spacer 230 is similar to the other embodiments discussed above. Specifically, the spacer includes a body 232, which may be made from any suitable material. In this embodiment, the spacer 230 includes a face plate 234 attached to a front side 236 of the spacer 230. The face plate 234 in this embodiment defines four first openings 238, 240, 242, 244 that connect to respective second openings 246, 248, 250, 252. Bores 254, 256, 258, 260 connect the respective openings to one another in the same manner as discussed in prior embodiments. The bores 254, 256, 258, 260 act cooperatively, in pairs, to provide both locking and compression, as in the prior-described embodiments. As in prior embodiments, the bores 254, 256, 258, 260 also are referred to as the first bore 254, the second bore 256, the third bore 258, and the fourth bore 260.

Concerning the face plate 234, the face plate 234 is contemplated to be made from a metal material. The metal may include steel, stainless, aluminum, titanium, alloys of any of these metals, among other materials that should be apparent to those skilled in the art. It is contemplated that the face plate 234 will be molded integrally with the body 232 of the spacer 230 so that the face plate 234 cannot be separated from the body 232 of the spacer. The integration of the face plate 234 to the spacer 232 may be accomplished by any means that should be apparent to those skilled in the art. It is also noted that the faceplate 234 defines fastener ports 262, 264, 266, 268, which are designed to receive and position fasteners therein.

Figure 19:
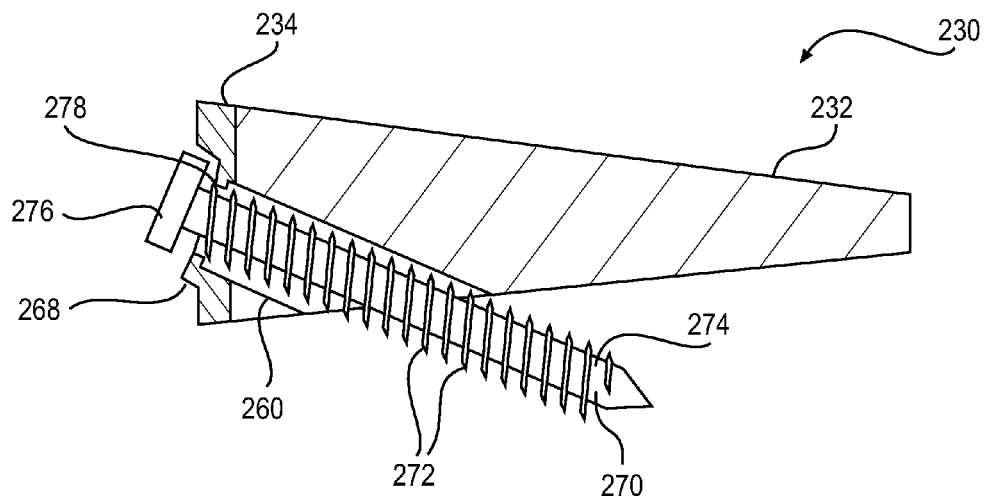
FIG. 19 is a cross-sectional side view of the spacer shown in FIG. 18, the cross-section being taken along the line 19-19 in FIG. 18.

FIG. 19 provides a cross-section of the spacer 230 illustrated in FIG. 18, the cross-section being taken along the line 19-19 in FIG. 18.

FIG. 19 illustrates a locking fastener 270 disposed in the fourth bore 260. As with the locking fastener 194, threads 272 extend along the entirety of the shaft 274. The locking fastener 270 also includes a head 276. As illustrated, the opening 244 in the face plate 234 is surrounded by a lip 278, which abuts against the head 276 of the locking fastener 270. This lip 278 assists with establishing a locking force, as discussed in greater detail below.

Figure 20:
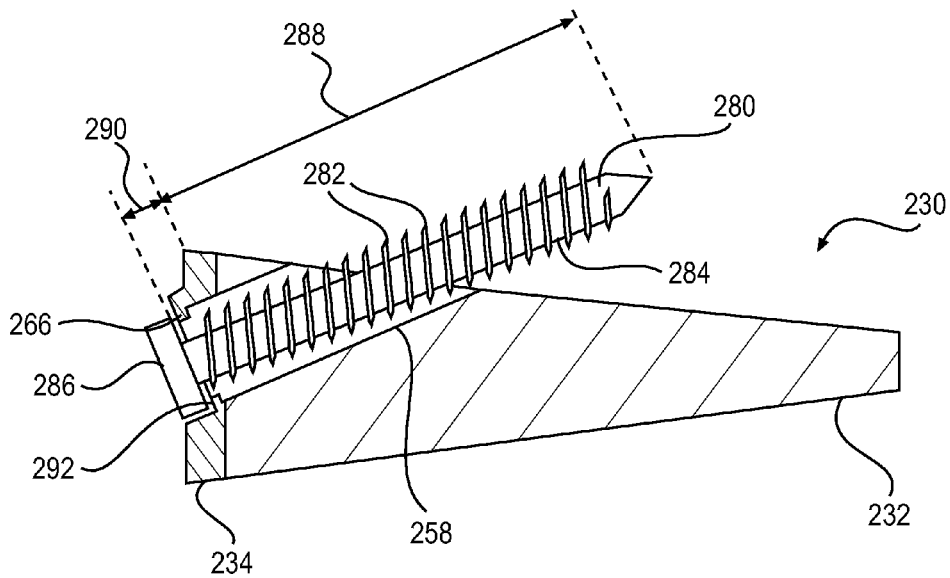
FIG. 20 is a cross-sectional side view of the spacer shown in FIG. 18, the cross-section being taken along the line 20-20 in FIG. 28.

FIG. 20 illustrates a compression fastener 280 disposed in the third bore 258. As with the compression fastener 204, the compression fastener 280 includes threads 282 disposed along a portion of the shaft 284. The compression fastener 280 also includes a head 286, as in prior embodiments. With reference to the threads 282, the threads extend along a threaded portion 288, but not along the unthreaded portion 290. The head 286 engages the lip 292 surrounding the first opening 242.

Cooperation between the fasteners 270, 280 will now be discussed in connection with FIGS. 19 and 20.

With respect to the spacer 230, locking and compressive forces are established between the face plate 234 and the adjacent vertebrae. With respect to the locking fastener 270, because the threads 272 extend to (or near to) the head 276, the threads engage the lip 278, thereby providing a securement against disengagement of the locking fastener 270. Similarly, the compression fastener 280 has an unthreaded portion 290 immediately adjacent to the head 286. As such, the threads 282 do not engage the lip 292. Instead, the head 286 applies pressure to the face plate 234 which, in turn, applies compression force between the spacer 230 and the adjacent vertebra.

In this embodiment, it is noted that the bores 254, 256, 258, 260 are larger than the width of the threads 272, 282 on the respective fasteners 270, 280. As such, in this illustrated embodiment, the threads 272, 282 do not also engage the spacer 230. As noted, the locking and compressive forces are applied via interaction with the lips 278, 292 provided on the face plate 234.

Figure 21:
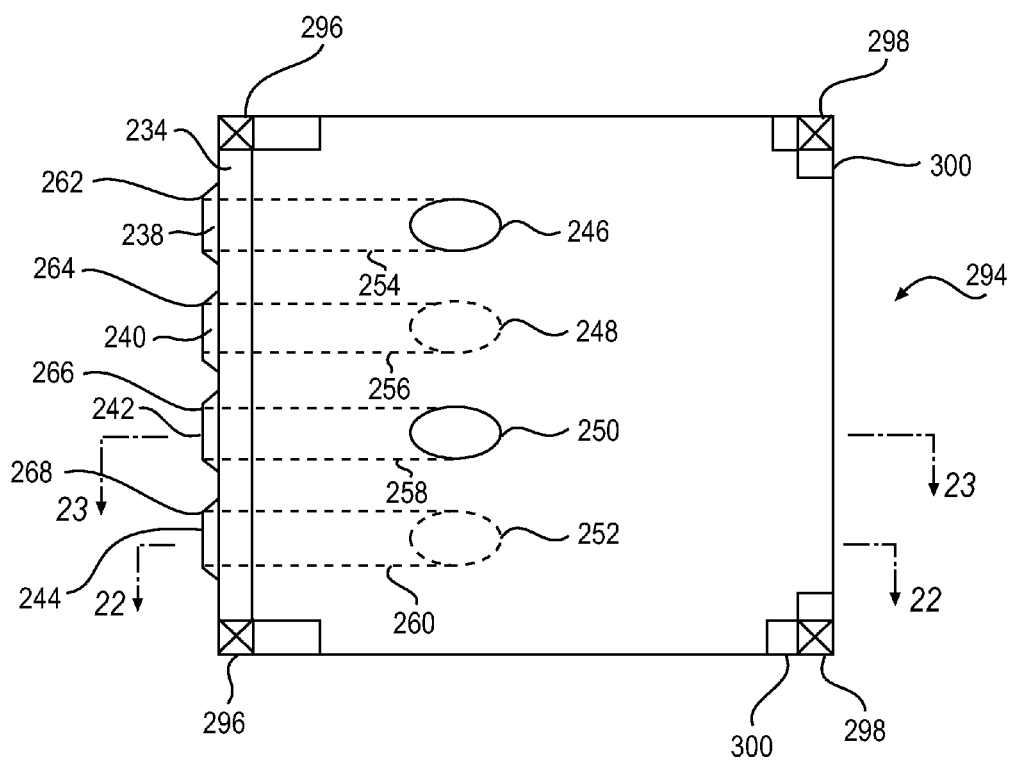
FIG. 21 is a top view of a ninth embodiment of the spacer of the present invention.
Figure 22:
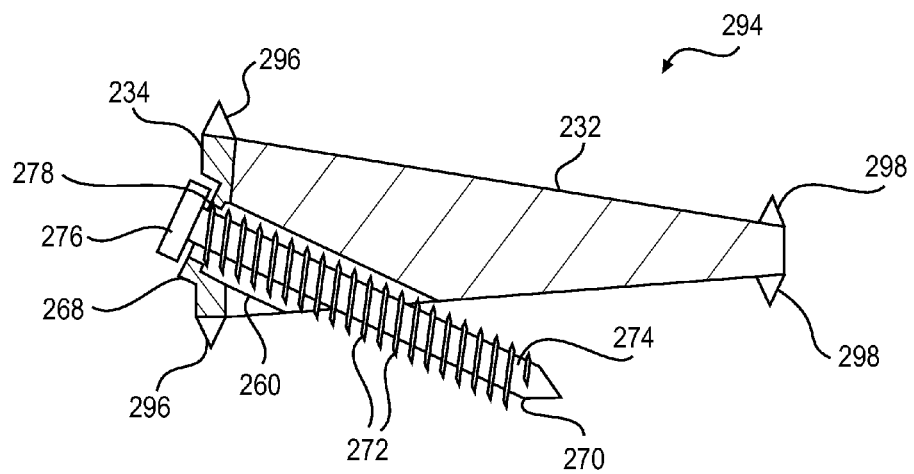
FIG. 22 is a cross-sectional side view of the spacer shown in FIG. 21, the cross-section being taken along the line 22-22 in FIG. 21.
Figure 23:
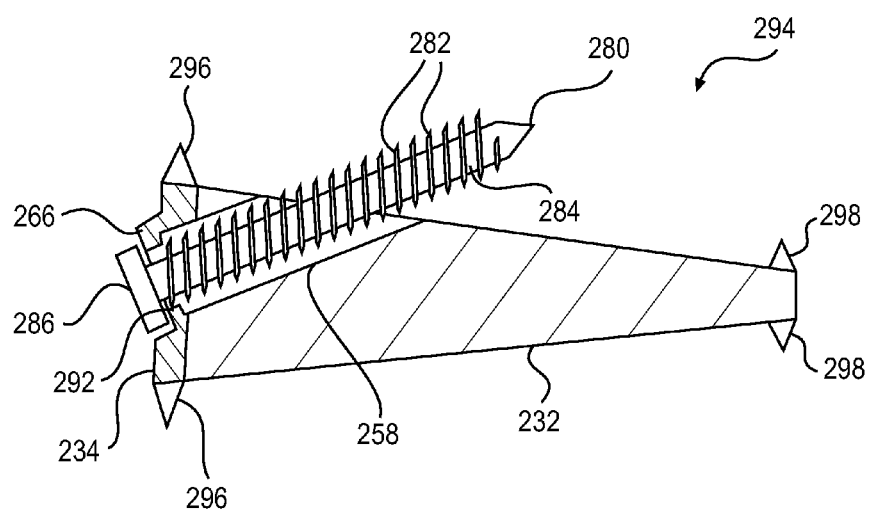
FIG. 23 is a cross-sectional side view of the spacer shown in FIG. 21, the cross-section being taken along the line 23-23 in FIG. 21.

FIG. 21 illustrates one further embodiment of the spacer 294 of the present invention. This embodiment of the spacer 294 is a variation of the spacer 230 described in connection with FIGS. 18-20. Accordingly, structures in the spacer 294 that are the same as in the spacer 230 are designated with the same reference numerals.

The spacer 294 adds front protrusions 296 and rear protrusions 298 to the body 232. The protrusions are contemplated to be made from a suitable material such as steel, stainless steel, titanium, or the like. As illustrated, the front protrusions 296 are integrally formed with the face plate 234. The rear protrusions 298 are connected to the spacer 294 via corner supports 300.

It is noted that the protrusions 296, 298 are contemplated to be about 0.25 mm in height, thereby increasing the total thickness of the spacer 294 by 0.50 mm. Other heights may be employed without departing from the scope of the present invention.

In addition, as with the protrusions 226, the protrusions 296, 298 are shown with a pyramidal shape. However any other shape, such as cubical, conical, ovoid, ellipsoidal, etc., may be employed without departing from the scope of the present invention.

It is contemplated that the various fasteners described will be made from a suitable metal material such as stainless steel or titanium. It is also contemplated that the fasteners will be about 6 mm in diameter. Other sizes of fasteners may be employed without departing from the scope of the present invention.

It is noted that the spacers 10, 54, 82, 110, 138, 164, 230, 294 are each illustrated with four bores. One pair of the bores extends to the top side of the spacer. The other pair of bores extends to the bottom side of the spacer. While four bores are illustrated, it is contemplated that a larger number of bores may be employed without departing from the present invention. If so, the larger number of bores need not be provided in pairs. For example, it is contemplated that a spacer may be provided with three bores extending to the top side and three bores extending to the bottom side. If so, two locking screws and one compression screw may be employed for each group of three bores. Still further variations are contemplated to fall within the scope of the present invention.

As noted above, the present invention is described in connection with several embodiments. The embodiments are not intended to be limiting of the present invention. To the contrary, the embodiments are intended to illustrate the scope and breadth of the present invention. Those skilled in the art should appreciate various equivalents and variations of the described embodiments. Those variations and equivalents are intended to by encompassed by the present invention.

What is claimed is:

1. A vertebral spacer, comprising:
    a body having a top side, a bottom side, a front side, and a rear side, wherein the top side is configured to be positioned adjacent to a first vertebra and the bottom side is configured to be positioned adjacent a second vertebra;
    a first bore extending from a first opening in the front side to a second opening on the top side;
    a second bore extending from a third opening in the front side to a fourth opening on the top side;
    a third bore extending from a fifth opening on the front side to a sixth opening on the bottom side;
    a fourth bore extending from a seventh opening on the front side to an eighth opening on the bottom side;
    first and second compression fasteners disposable in the first and third bores, wherein each compression fastener includes a shaft and threads disposed along a portion of the shaft, the threads are bone-engaging threads, the bone-engaging threads are engageable with the first or second vertebra, and the remainder of the shaft excludes threads;
    first and second locking fasteners disposable in the second and fourth bores, wherein each locking fastener includes a shaft and threads disposed therealong, a portion of the threads are bone-engaging threads, a portion of the threads are body-engaging threads, the bone-engaging threads are engageable with the first or second vertebra, and the body-engaging threads are engageable with the body; and
    at least four protrusions disposed on the top side and at least four protrusions disposed on the bottom side, each of the protrusions disposed at corners of the body, the at least eight protrusions being engageable with the first and second vertebrae,
    wherein the first compression fastener is configured to apply a first predetermined compression force between the body and the first vertebra and the first locking fastener cooperates with the first compression fastener to lock the body to the first vertebra at the first predetermined compression force,
    wherein the second compression fastener is configured to apply a second predetermined compression force between the body and the second vertebra and the second locking fastener cooperates with the second compression fastener to lock the body to the second vertebra at the second predetermined compression force,
    wherein the first compression fastener and the first locking fastener, disposed adjacent to one another, are configured to work together as a first pair of fasteners to apply the first predetermined compression force and lock the body to the first vertebra at the first predetermined compression force after the first compression fastener and the first locking fastener are fully inserted into the body,
    wherein the second compression fastener and the second locking fastener, disposed adjacent to one another, are configured to work together as a second pair of fastener to apply the second predetermined compression force and lock the body to the second vertebra at the second predetermined compression force after the second compression fastener and the second locking fastener are fully inserted into the body, and
    wherein the first opening, the third opening, the fifth opening, and the seventh opening are disposed in line with one another on the front side of the body between the top side and the bottom side.

2. The vertebral spacer of claim 1, wherein the top side and the bottom side of the body are substantially parallel to one another.

3. The vertebral spacer of claim 1, wherein at least one of the top side or the bottom side are disposed at a first angle of between about 10° to 20° from a horizontal plane extending through the body.

4. The vertebral spacer of claim 3, wherein the first angle is about 15° from the horizontal plane.

5. The vertebral spacer of claim 1, wherein each of the first bore, the second bore, the third bore, and the fourth bore are disposed at a second angle of between about 40° to 65° from a horizontal plane extending through the body.

6. The vertebral spacer of claim 5, wherein the second angle is between about 40° to 50° from the horizontal plane.

7. The vertebral spacer of claim 6, wherein the second angle is about 45°.

8. The vertebral spacer of claim 5, wherein the second angle is between about 55° to 65° from the horizontal plane.

9. The vertebral spacer of claim 8, wherein the second angle is about 60°.

10. The vertebral spacer of claim 1, further comprising:
    a fifth bore extending from a ninth opening in the front side to a tenth opening on the top side; and
    a sixth bore extending from an eleventh opening on the front side to a twelfth opening on the bottom side.

11. The vertebral spacer of claim 10, wherein compression fasteners are disposable in the fifth and sixth bores.

12. The vertebral spacer of claim 10, wherein locking fasteners are disposable in the fifth and sixth bores.

13. The vertebral spacer of claim 1, wherein the body includes at least one recess in register with at least one of the bores to accommodate a head on a fastener disposable in the at least one of the bores.

14. The vertebral spacer of claim 1, further comprising:
    a face plate disposed on the body, at the front side, the face plate defining the first, third, fifth, and seventh openings.

15. The vertebral spacer of claim 14, wherein the face plate is integrally molded with the body.

16. The vertebral spacer of claim 14, wherein the face plate comprises a metal or metal alloy suitable for placement in a living organism.

17. The vertebral spacer of claim 14, wherein the face plate further defines a lip surrounding each of the first, third, fifth, and seventh openings.

18. The vertebral spacer of claim 17, wherein each compression fastener comprises a head adjacent to a non-threaded portion, each head engaging a respective lip so as to be configured to apply compression between the body and an adjacent vertebra.

19. The vertebral spacer of claim 17, wherein each locking fastener Comprises a head adjacent to a threaded portion, each threaded portion engaging a respective lip so as to be configured to apply a locking force between the body and an adjacent vertebra.

* * * * *